(12) United States Patent
Maurer et al.

(10) Patent No.: US 7,780,978 B2
(45) Date of Patent: *Aug. 24, 2010

(54) ORAL PHARMACEUTICAL COMPOSITIONS AND METHODS OF USING THE SAME

(75) Inventors: Barry J. Maurer, Sylmar, CA (US); Charles Patrick Reynolds, Sherman Oaks, CA (US); David W. Yesair, Byfield, MA (US); Robert Travis McKee, Jacksonville, FL (US); Stephen W. Burgess, Chelsea, AL (US); Walter A. Shaw, Birmingham, AL (US)

(73) Assignee: Childrens Hospital Los Angeles, Los Angeles, CA (US)

( * ) Notice: Subject to any disclaimer, the term of this patent is extended or adjusted under 35 U.S.C. 154(b) by 1315 days.

This patent is subject to a terminal disclaimer.

(21) Appl. No.: 11/170,561

(22) Filed: Jun. 29, 2005

(65) Prior Publication Data
US 2006/0008508 A1 Jan. 12, 2006

Related U.S. Application Data

(63) Continuation-in-part of application No. 10/767,352, filed on Jan. 30, 2004.

(60) Provisional application No. 60/444,530, filed on Jan. 31, 2003.

(51) Int. Cl.
*A61K 47/00* (2006.01)
*A61K 31/16* (2006.01)
*A23L 1/308* (2006.01)

(52) U.S. Cl. .......................... 424/439; 514/613; 426/72

(58) Field of Classification Search ................. 424/439; 514/449, 613; 426/72
See application file for complete search history.

(56) References Cited

U.S. PATENT DOCUMENTS

| 4,665,098 | A | * | 5/1987 | Gibbs et al. ................. 514/613 |
| 4,874,795 | A | * | 10/1989 | Yesair ........................ 514/725 |
| 5,891,466 | A | | 4/1999 | Yesair |
| 6,207,194 | B1 | * | 3/2001 | Glahn ........................ 424/489 |
| 6,225,325 | B1 | * | 5/2001 | Jacob ......................... 514/328 |
| 6,254,853 | B1 | * | 7/2001 | Hendler et al. ................ 424/45 |
| 2002/0156023 | A1 | * | 10/2002 | Walling et al. ................ 514/27 |

FOREIGN PATENT DOCUMENTS

WO  WO 03/031593 A2  4/2003

OTHER PUBLICATIONS

Lepage et al. "Effect of an organized lipid matrix on lipid absorption and clinical outcomes in patients with cystic fibrosis", *The Journal of Pediatrics* 141(2):178-185 (2002).
Supplementary European Search Report corresponding to European Patent Application No. 04706566.9 dated Apr. 22, 2010.

* cited by examiner

*Primary Examiner*—Blessing M Fubara
(74) *Attorney, Agent, or Firm*—Myers Bigel Sibley & Sajovec, PA

(57) ABSTRACT

The present invention provides an edible composition for oral delivery of an active agent such as paclitaxel or a retinide. The composition comprises, in the form of a dry flowable powder: (a) an active agent such as a retinide; (b) lipid matrix composition; (c) optionally sweetener; (d) flour. Compositions of the invention may be administered per se or mixed with a solid or liquid food carrier, for direct oral consumption by a subject or administration through a feeding tube.

19 Claims, 2 Drawing Sheets

ORAL PHARMACEUTICAL COMPOSITIONS AND METHODS OF USING THE SAME

RELATED APPLICATIONS

This application is a continuation-in-part of U.S. patent application Ser. No. 10/767,352, filed Jan. 30, 2004, which in turn claims the benefit of provisional application Ser. No. 60/444,530, filed Jan. 31, 2003, the disclosures of both of which are incorporated by reference herein in their entirety.

RELATED APPLICATION INFORMATION

Statement of Government Support

This invention was made with Government support under grant number CA081403, CA082830, and CA100895 from the National Cancer Institute. The Government has certain rights to this invention.

FIELD OF THE INVENTION

The present invention concerns pharmaceutical compositions for oral delivery of a retinide such as fenretinide.

BACKGROUND OF THE INVENTION

Fenretinide [HPR; all-trans-N-(4-hydroxyphenyl)retinamide; CAS Registry number 65646-68-6] is a synthetic retinoic acid derivative having the structure:

Fenretinide is minimally soluble in aqueous solution. U.S. Pat. No. 4,665,098 by Gibbs describes an oral pharmaceutical composition of fenretinide as useful for the treatment of breast and bladder cancer. However, the bioavailability of this oral fenretinide composition is limited and greater anticancer effects might be obtained if fenretinide could be delivered intravenously to achieve higher drug plasma levels. Hence, there currently remains a need for new pharmacological compositions of fenretinide, especially for oral administration which provide for both satisfactory solubility, and plasma and tissue bioavailability, especially in patient populations generally less tolerant of capsule, tablet, or other non-chewable or non-imbibible drug delivery vectors.

Intravenous formulations of 4-HPR have recently been developed that obtain significantly higher 4-HPR plasma (30-120 µM) and tissue levels in rodent and canine animal models than the current oral capsule formulation while retaining minimal systemic toxicity (results not shown). However, this formulation is intended for use in the inpatient setting in conjunction with intravenous safingol (used as a ceramide metabolism modulator). Thus, there remains a need for an improved oral formulation of 4-HPR for outpatient use, such as in maintenance therapy during states of minimal residual disease, or in the palliative care setting, that is easier to administer and that has improved bioavailability. Such a formulation would be particularly advantageous for small children and elderly adults in which compliance with the schedules of the current oral capsular 4-HPR is problematical. Further, an improved oral formulation would facilitate the combination of 4-HPR with ceramide modulating agents in the outpatient setting.

Formulations of fenretinide suitable for high dose parenteral delivery are described in PCT Application WO 02/05869 to Gupta et al.

Formulations of fenretinide suitable for oral delivery are described in U.S. Pat. No. 5,972,911 and U.S. Pat. No. 4,874,795.

SUMMARY OF THE INVENTION

The present invention provides an edible composition for oral delivery of an active agent such as a retinide. The composition comprises or consists essentially of, in the form of a dry flowable powder:

(a) an active agent such as a retinide (including a single active agent, or two or more active agents in combination), preferably in an amount by weight of from 1 to 10 or 20 percent;

(b) lipid matrix composition, preferably in an amount by weight of from 5 to 40 percent (the composition preferably being one comprising or consisting essentially of at least one fatty acid, at least one monoglyceride, and lysophosphatidylcholine, and the lipid matrix composition preferably containing not more than 7 or 8 moles water per mole of lipid matrix);

(c) optionally sweetener, which when present may be included in an amount by of from 1 to 30 percent;

(d) flour, preferably in an amount of from 20 to 80 percent by weight; and (e) optionally humectant, in an amount by weight of from 0 or 1 to 16 percent.

In one preferred embodiment, the lipid matrix composition may comprise (i) at least one non-esterified fatty acid (e.g., one having 14 to 22 carbon atoms), (ii) at least one monoglyceride which is a monoester of glycerol and a fatty acid (e.g., the fatty acid having 14 to 22 carbon atoms), and (iii) lysophosphatidylcholine (e.g., one in which in which the fatty acid moiety has 14 to 22 carbon atoms). The fatty acids and monoglycerides may together comprise from 60 or 70 mole percent to 99 mole percent of the lipid matrix composition. The molar ratio of the fatty acids to the monoglycerides may be from 4:1 or 2:1 to 1:2 or 1:4. The lysophosphatidylcholine may comprise from 1 mole percent to 30 or 40 mole percent of the lipid matrix composition.

As discussed in greater detail below, compositions of the invention may be packaged in bulk or unit dosage form. Compositions of the invention may be administered per se or mixed with a solid or liquid food carrier, for direct oral consumption by a subject or administration through a feeding tube.

Thus, a further aspect of the present invention is a method of treating a disorder such as a proliferative disease in a subject in need thereof, comprising feeding or administering the subject a composition as described above in an amount effective to treat that disorder (such as a proliferative disease).

A still further aspect of the present invention is the use of an active agent as described herein for the preparation of a composition as described herein.

In particular embodiments of the foregoing, at least two active agents are included in the composition. In some embodiments the first active agent is a retinide (e.g., fenretinide) and the second active agent is a glucosylceramide synthase inhibitor (e.g., 1-phenyl-2-palmitoylamino-3-morpholino-1-propanol (PPMP)).

PCT Application WO 03/031593 describes acidified, protonated aqueous, predominantly inverse hexagonal phase LYM-X-SORB™ compositions containing proteins, sugars and starches as a nutritional supplement but does not suggest the use or formulation of non-acidic, minimally hdyrated, predominantly lamellar phase LYM-X-SORB™ compositions containing proteins, sugars and/or starches for administering active agents such as fenretinide.

The foregoing and other objects and aspects of the present invention are explained in greater detail in the drawings herein and the specification set forth above.

BRIEF DESCRIPTION OF DRAWINGS

FIG. 1. Comparison of 4-HPR in LXS matrix vs Capsule Formulation at 120 mg/kg/day. Cohorts of five mice were feed with 120 mg/kg/day of 4-HPR formulated in various LXS compositions, or 4-HPR expressed from capsules, mixed with mouse chow or Slim-Fast®, divided BID, ×4.5 days. Animals were sacrificed 3 hrs after the last dose and 4-HPR levels in plasma and tissues were assayed by HPLC. Results showed that certain LXS formulations obtained higher levels than the 4-HPR capsule formulation. PLASMA: G1 vs capsule, P=0.006; LYM-X 5.59 vs capsule, P=0.06; LIVER: G1 vs capsule, P=0.013; LYM-X 5.59 vs capsule, P=0.045; LUNGS: G1 vs capsule, P=0.028; G2 vs capsule, P=0.05; KIDNEY: G1 vs capsule, P=0.007; LYM-X 5.59 vs capsule, P=0.06; BRAIN: G1 vs capsule, P=0.01; LYM-X 5.58 vs capsule, P=0.02. Statistical analysis by Student's t-test. Columns, in each set of columns, in sequence from left to right, represent LYM-X 5.57, LYM-X 5.58, LYM-X 5.60, LYM-X 5.59, Capsule Lot #R-6124, LYM-X 5.60 G1 (SLIM-FAST™), and LYM-X 5.60 G2 (DI Water).

FIG. 2. Comparison of 4-HPR in LXS™ matrix vs Capsule Formulation at 250 mg/kg/day. Cohorts of five mice were gavaged with 250 mg/kg/day of 4-HPR in LXS formulation LYM-X 5.60 in Slim-Fast® or in water, or 4-HPR expressed from capsules and mixed in Slim-Fast®, divided BID, ×4.5 days. Animals were sacrificed 3 hrs after the last dose and 4-HPR levels in plasma and tissues were assayed by HPLC. Results showed that LXS formulations, especially in Slim-Fast®, obtained significantly higher levels than the 4-HPR capsule formulation except in brain tissue. PLASMA: G1 vs capsule, P=0.006; G2 vs capsule, P=0.008; LIVER: G1 vs capsule, P=0.001; G2 vs capsule, P=0.01; LUNGS: G1 vs capsule, P=0.05; G2 vs capsule, P=0.035; KIDNEY: G1 vs capsule, P=0.013; G2 vs capsule, P=0.22; BRAIN: G1 vs capsule, P=0.187; G2 vs capsule, P=0.11. Statistical analysis by Student's t-test. PLEASE NOTE CHANGE OF SCALE. Columns, in each set of columns, in sequence from left to right, represent LYM-X 5.60 GI (SLIMFAST™), LYM-X 5.60 G2 (DI Water), and 4-HPR Capsule in SLIMFAST™

FIG. 3. Comparison of 4-HPR in LXS™ matrix vs Capsule Formulation at 560 mg/kg/day. In a pilot experiment, single mice were gavaged with 560 mg/kg/day of 4-HPR formulated in various LXS compositions or 4-HPR expressed from 4-HPR capsules, divided BID, ×4.5 days. Animals were sacrificed 3 hrs after the last dose and 4-HPR levels in plasma and tissues were assayed by HPLC. Results showed that all LXS formulations apparently obtained much higher levels than the capsule formulation in plasma and liver and lung tissues, and LYM-X 5.60 exceeded capsule levels in kidney tissue. 4-HPR levels achieved in brain tissue using compositions LYM-X 5.59 and LYM-X 5.60 were about double that obtained using the capsule formulation. Columns, in each set of columns, in sequence from left to right, represent LYM-X 5.57, LYM-X 5.58, LYM-X 5.60, LYM-X 5.59, and Capsule Lot #R-6124.

DETAILED DESCRIPTION OF THE PREFERRED EMBODIMENTS

The present invention is explained in greater detail below. Applicants specifically intend that all United States patents cited herein be incorporated herein by reference in their entirety.

1. Active Agents.

While the present invention is initially concerned with the delivery of retinides, a variety of different active agents can be used in carrying out the present invention. Examples of active agents that can be incorporated into the compositions and formulations of the present invention include, but are not limited to, paclitaxel, insulin, histrelin, β estradiol, nifedipin analogues, hydrochlorothiazide, McN-5703, capsaicin, diltiazen, renin inhibitors, hydrocortisone, cromolyn, pramoxine, buprenorphine, progesterone, cyclosporin A, metronidazole, and gentamicin. Retinides, particularly fenretinide, are currently preferred. Thus active agents are, in preferred embodiments, antineoplastic agents, as discussed further below.

Retinides. Retinides used for carrying out the present invention are, in general, ceramide-generating retinoids or retinoic acid derivatives. Such compounds include those described in U.S. Pat. No. 4,190,594 to Gander (the disclosures of all patent references cited herein are incorporated herein by reference). Ceramide-generating retinoids include all trans-retinoic acid (ATRA) and retinoic acid derivatives, including but not limited to:

(A) esters of all-trans-retinoic acid having the following formula:

wherein X is a member selected from the group consisting of:

2-cyclohexylethyl; 10-carbomethoxydecyl; 4-hydroxybutyl; cholesteryl; mixed m- and p-vinylbenzyl; and 4-bromobenzyl;

(B) esters of all-trans-retinoic acid having the following formula:

wherein Y is a member selected from the group consisting of: cholesteryloxy; phenyl; 4-bromophenyl; 4-methoxyphenyl; 4-nitrophenyl; 4-hydroxyphenyl; 4-methylphenyl; 4-cyanophenyl; 4-ethoxyphenyl; 4-acetoxyphenyl; 2-naphthyl; 4-biphenyl; 2,5-dimethoxyphenyl; 2,4-dichlorophenyl; 2,4-dimethylphenyl; 3,4-diacetoxyphenyl; 3,4,5-trimethoxyphenyl; and 2,4,6-trimethylphenyl; and

(C) amides of all-trans-retinoic acid having the following formula:

wherein Z is a member selected from the group consisting of: n-propylamino; tert-butylamino; 1,1,3,3-tetramethylbutylamino; 1-morpholino; 4-hydroxyphenylamino; 4-carbomethoxy-2-hydroxyphenylamino; beta-(3,4-dimethoxyphenyl)-ethylamino; 2-benzothiazolylamino; 1-imidazolyl; 1-(2-nicotinoylhydrazolyl); 1-benzotriazolyl; 1-(1,2,4-triazolyl);

Particularly preferred is all-trans-N-(4-hydroxyphenyl)retinamide, also called fenretinide, which has CAS registry number 65646-68-6, and has the structure:

The foregoing compounds can be prepared in accordance with known techniques. See, e.g., U.S. Pat. No. 4,190,594 to Gander et al.; U.S. Pat. No. 4,665,098 to Gibbs.

Additional retinoic acid derivatives that can be used to carry out the present invention include C-Glycoside analogs of N-(4-hydroxyphenyl)retinamide-O-glucuronide. Such compounds and their preparation are known and described in U.S. Pat. Nos. 5,663,377 and 5,599,953, both to Curley et al., the disclosures of which are incorporated by reference herein in their entirety. Such compounds may have the general formula:

where R is COOH, $CH_2OH$, or H, and n is 0 or 1.

Specific examples of such compounds include: 4-(retinamido)phenyl-C-glucuronide; 4-(retinamido)phenyl-C-glucoside; 4-(retinamido)phenyl-C-xyloside; 4-(retinamido)benzyl-C-glucuronide; 4-(retinamido)benzyl-C-glucoside; 4-(retinamido)benzyl-C-xyloside; 1-($\beta$-D-glucopyranosyl)retinamide; and 1-(D-glucopyranosyluronosyl) retinamide.

A. Glucosylceramide synthesis and 1-acylceramide synthesis inhibitors. The composition may also include a glycosylceramide synthesis and/or a 1-acylceramide synthesis inhibitor as an active agent. In one embodiments such compounds are preferably included in combination with a retinide as discussed above. By "and/or" is meant that either of two drugs with a selective activity for one or the other enzyme may be administered singly or in combination, or a single drug active in inhibiting both enzymes may be given. Examples of such compounds include, but are not limited to, compounds having the formula:

where R is an aromatic ring such as phenyl, a cyclohexyl group, or an alpiphatic group having 10 to 15 carbon atoms, $R_1$ is an amine group such as a morpholino group; and n is an integer of from 4 to 18 (including functional homologues, isomers and pharmaceutically acceptable salts thereof. Preferably, n is 4, 6, 8, 10, 12 or 14, and the D enantiomers of such compounds are preferred. In another embodiment the threo enantiomers of such compounds are preferred. In another embodiment, the D, threo enantiomer of such compounds are preferred. Such compounds are known and are disclosed, for example, in U.S. Pat. No. 5,302,609 to Shayman and Radin; U.S. Pat. No. 5,041,441 to Radin et al.; and U.S. Pat. No. 5,707,649 to Inokuchi et al. Specific examples of glucosylceramide synthase inhibitors include:

1-phenyl-2-acylamino-3-morpholino-1-propanol in which n is 6 to 12;

1-phenyl-2-decanoylamino-3-morpholino-1-propanol (PDMP);

1-phenyl-2-palmitoylamino-3-morpholino-1-propanol (PPMP); and

Tamoxifen, including tamoxifen citrate.

Additional active agents. Still more active agents (particularly including antineoplastics agents) that may be used in the present invention include, but are not limited to, those described in U.S. Pat. No. 6,858,598 (Searle)

The phrase "antineoplastic agents" includes agents that exert antineoplastic effects, i.e., prevent the development, maturation, or spread of neoplastic cells, directly on the tumor cell, e.g., by cytostatic or cytocidal effects, and not indirectly through mechanisms such as biological response modification. There are large numbers of antineoplastic agents available in commercial use, in clinical evaluation and in pre-clinical development, which could be included in the present invention for treatment of neoplasia by combination drug chemotherapy. For convenience of discussion, antineoplastic agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors DHA derivatives, DNA topoisomerase, endostatin, epipodophylotoxins, genistein, hormonal anticancer agents, hydrophilic bile acids (URSO), immunomodulators or immunological agents, integrin antagonists interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids selective inhibitors of proliferation and migration of endothelial cells, selenium, stromelysin inhibitors, taxanes, vaccines, and vinca alkaloids.

The major categories that some preferred antineoplastic agents fall into include antimetabolite agents, alkylating agents, antibiotic-type agents, hormonal anticancer agents, immunological agents, interferon-type agents, and a category of miscellaneous antineoplastic agents. Some antineoplastic agents operate through multiple or unknown mechanisms and can thus be classified into more than one category.

A first family of antineoplastic agents which may be used in combination with the present invention consists of antimetabolite-type antineoplastic agents. Antimetabolites are typically reversible or irreversible enzyme inhibitors, or compounds that otherwise interfere with the replication, translation or transcription of nucleic acids. Suitable antimetabolite antineoplastic agents that may be used in the present invention include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine, fludarabine phosphate, N-(2'-furanidyl)-5-fluorouracil, Daiichi Seiyaku FO-152, fluorouracil (5-FU), 5-FU-fibrinogen, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate; Takeda TAC-788, thioguanine, tiazofurin, Erbamont TIF, trimetrexate, tyrosine kinase inhibitors, tyrosine protein kinase inhibitors, Taiho UFT, toremifene, and uricytin.

A second family of antineoplastic agents which may be used in combination with the present invention consists of alkylating-type antineoplastic agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. Suitable alkylating-type antineoplastic agents that may be used in the present invention include, but are not limited to, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517 estramustine phosphate sodium, etoposide phosphate, fotemustine, Unimed G-6-M. Chinoin GYKI-17230, hepsulfam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromustine, Tanabe Seiyaku TA-077, tauromustine, temozolomide, teroxirone, tetraplatin and trimelamol.

A third family of antineoplastic agents which may be used in combination with the present invention consists of antibiotic-type antineoplastic agents. Suitable antibiotic-type antineoplastic agents that may be used in the present invention include, but are not limited to Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen; elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with the present invention consists of synthetic nucleosides. Several synthetic nucleosides have been identified that exhibit anticancer activity. A well known nucleoside derivative with strong anticancer activity is 5-fluorouracil (5-FU). 5-Fluorouracil has been used clinically in the treatment of malignant tumors, including, for example, carcinomas, sarcomas, skin cancer, cancer of the digestive organs, and breast cancer. Derivatives of 5-fluorouracil with anti-cancer activity have been described in U.S. Pat. No. 4,336,381.

U.S. Pat. No. 4,000,137 discloses that the peroxidate oxidation product of inosine, adenosine, or cytidine with methanol or ethanol has activity against lymphocytic leukemia. Cytosine arabinoside (also referred to as Cytarabin, araC, and Cytosar) is a nucleoside analog of deoxycytidine that was first synthesized in 1950 and introduced into clinical medicine in 1963. 5-Azacytidine is a cytidine analog that is primarily used in the treatment of acute myelocytic leukemia and myelodysplastic syndrome. 2-Fluoroadenosine-5'-phosphate (Fludara, also referred to as FaraA) is one of the most active agents in the treatment of chronic lymphocytic leukemia.

A fifth family of antineoplastic agents which may be used in combination with the present invention consists of hormonal agents. Suitable hormonal-type antineoplastic agents that may be used in the present invention include, but are not limited to Abarelix; Abbott A-84861; Abiraterone acetate; Aminoglutethimide; anastrozole; Asta Medica AN-207; Antide; Chugai AG-041R; Avorelin; aseranox; Sensus B2036-PEG; Bicalutamide; buserelin; BTG CB-7598, BTG CB-7630; Casodex; cetrolix; clastroban; clodronate disodium; Cosudex; Rotta Research CR-1505; cytadren; crinone; deslorelin; droloxifene; dutasteride; Elimina; Laval University EM-800; Laval University EM-652; epitiostanol; episteride; Mediolanum EP-23904; EntreMed 2-ME; exemestane; fadrozole; finasteride; flutamide; formestane; Pharmacia & Upjohn FCE-24304; ganirelix; goserelin; Shire gonadorelin agonist; Glaxo Wellcome GW-5638; Hoechst Marion Roussel Hoe-766; NCI hCG; idoxifene; isocordoin; Zeneca ICI-182780; Zeneca ICI-118630; Tulane University J015X; Schering Ag J96: ketanserin; lanreotide; Milkhaus LDI-200; letrozol; leuprolide; leuprorelin; liarozole; lisuride hydrogen maleate; loxiglumide; mepitiostane; Leuprorelin; Ligand Pharmaceuticals LG-1127; LG-1447; LG-2293; LG-2527; LG-2716; Bone Care International LR-103; Lilly LY-326315; Lilly LY-353381-HC1; Lilly LY-326391; Lilly LY-353381; Lilly LY-357489; miproxifene phosphate; Orion Pharma MPV-2213ad; Tulane University MZ-4-71; nafarelin; nilutamide; Snow Brand NKS01; octreotide; Azko Nobel ORG-31710; Azko Nobel ORG-31806; orimeten; orimetene; orimetine; ormeloxifene; osaterone; Smithkline Beecham SKB-105657; Tokyo University OSW-1; Peptech PTL-03001; Pharmacia & Upjohn PNU-156765; quinagolide; ramorelix; Raloxifene; statin; sandostatin LAR; Shionogi S-10364; Novartis SMT-487; somavert; somatostatin; tamoxifen; tamoxifen methiodide; teverelix toremifene; triptorelin; TT-232; vapreotide; vorozole; Yamanouchi YM-116; Yamanouchi YM-511; Yamanouchi YM-55208; Yamanouchi YM-53789; Schering AG ZK-1911703; Schering AG ZK-230211; and Zeneca ZD-182780.

A sixth family of antineoplastic agents which may be used in combination with the present invention consists of a miscellaneous family of antineoplastic agents including, but not limited to alpha-carotene, alpha-difluoromethyl-arginine, acitretin, Biotec AD-5, Kyorin AHC-52, alstonine, amonafide, amphethinile, amsacrine, Angiostat, ankinomycin, antineoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, dacarbazine, datelliptinium, DFMO, didemnin-B, dihaematoporphyrin ether, dihydrolenperone dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, Eulexin.RTM., Cell Pathways Exisulind.RTM. (sulindac sulphone or CP-246), fenretinide, Merck Research Labs Finasteride, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron; Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, Encore Pharmaceuticals R-flurbiprofen, Sandostatin; Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, selenium(selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione. Suntory SUN 0237, Suntory SUN 2071, Sugen SU-101, Sugen SU-5416, Sugen SU-6668, sulindac, sulindac sulfone; superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, Zileuton, ursodeoxycholic acid, and Zanosar.

Still more preferred antineoplastic agents include: anastrozole, calcium carbonate, capecitabine, carboplatin, cisplatin, Cell Pathways CP-461, cyclophosphamide, docetaxel, doxorubicin, etoposide, Exisulind®, fluorouracil (5-FU), fluoxymestrine, gemcitabine, goserelin, irinotecan, ketoconazole, letrozol, leucovorin, levamisole, megestrol, mitoxantrone, paclitaxel, raloxifene, retinoic acid, tamoxifen, thiotepa, topotecan, toremifene, vinorelbine, vinblastine, vincristine, selenium (selenomethionine), ursodeoxycholic acid, sulindac sulfone and eflornithine (DFMO).

"Antineoplastic agents" as used herein includes compounds that, while not active as antineoplastic agents when administered by themselves, enhance the activity of another active agent when administered in combination with that other active agent (that is "enhancers" or "enhancers of antineoplastic agents"). Examples include inhibitors of the P-glycoprotein (MDR1 drug efflux protein (or "multiple drug resistance inhibitors"), such as cyclosporine or PSC833, combined with a drug that is a substrate of the p-glycoprotein pump, such as doxorubicin or vincristine. Such compounds are kown and described in, for example, U.S. Pat. Nos. 6,210,917; 5,416,091; 5,300,282; 5,124,339; 5,124,338; and 5,114,951.

2. Lipid Matrix Compositions.

Lipid matrix compositions that may be used to carry out the present invention generally comprise a combination of lysophosphatidylcholine, monoglyceride, and fatty acid. Without wishing to be bound to any particular theory of the invention, it is believed that the lipid matrix composition is non-liposomal (e.g., in a lamellar phase, and non- or minimally-hexagonal phase and/or inverse hexagonal phase) and forms an organized lipid matrix of lysophosphatidylcholine, monoglyceride and fatty acid that enfolds the active agent in acyl-constituents of the lipid matrix monomer backbones for absorption in the proximal intestine, with the monomers forming chylomicron-like elements that enter systemic circulation via the thoracic duct.

Lipid matrix compositions suitable for use in carrying out the present invention are known and described in, for example, U.S. Pat. No. 4,874,795; U.S. Pat. No. 5,891,466; U.S. Pat. No. 5,972,911; U.S. Pat. No. 6,426,069; and PCT Application WO 03/031593, the disclosures of which applicant specifically intends be incorporated by reference herein in their entirety. In one embodiment useful for carrying out the present invention, the lipid matrix composition comprises:

(a) at least one non-esterified fatty acid having 14 to 18, or 14 to 22, carbon atoms (e.g., palmitoleic, oleic, linoleic, or linolenic fatty acids);

(b) at least one monoglyceride which is a monoester of glycerol and a fatty acid having 14 to 18, or 14 to 22, carbon atoms (e.g., palmitoleic, oleic, linoleic, or linolenic fatty acids); and (c) lysophosphatidylcholine in which the fatty acid moiety has 14 to 18, or 14 to 22, carbon atoms (e.g., in which the fatty acid moiety is a palmitoleic, oleic, linoleic, or linolenic fatty acid).

In general, the fatty acids and monoglycerides together may comprise from about 70 mole percent to about 99 mole percent of the lipid matrix composition, the molar ratio of the fatty acids to the monoglycerides may be from about 2:1 to about 1:2, and the lysophosphatidylcholine may comprises from about 1 mole percent to about 30 mole percent of the lipid matrix composition.

The lipid matrix compositions may be nonaqueous or minimally hydrated (e.g., containing less than 5, 6, 7 or 8, and preferably not more than 1, 2, 3 or 4, Moles of water per mole of lipid matrix composition). The lipid matrix composition may be in the form of colloidal particles. Where minimally aqueous the compositions may further comprise (d) bicarbonate (e.g., wherein the concentration of the lysophosphatidylcholine is at least 0.1 mM in the minimally aqueous environment and the molar ratio of the bicarbonate to the lysophosphatidylcholine is greater than 1:1, greater than 1.4:1, or greater than 7:1), and optionally may further comprise (e) bile salts such as sodium taurocholate (e.g., wherein the molar ratio of the bile salts to the lysophosphatidylcholine may be at least 10:1).

A particularly preferred composition for combination with the active agent is LYM-X-SORB™ drug matrix composition (see, e.g., G. Lepage, D. Yesair et al., *J. Pediatrics* 141, 178-185 (2002)), available from BioMolecular Products, Inc., 136 Main Street, Byfield, Mass. 01922 USA (telephone 978-462-2244) or Avanti Polar Lipids, Inc., 700 Industrial Park Drive, Alabaster, Ala. 35007 USA (telephone 205-663-24924; fax 205-663-0756) in a non-acidified and non-protonated and non-aqueous lipid matrix form (e.g., minimally hydrated) of predominantly lamellar phase and with minimal hexagonal or inverse hexagonal phase.

The active agent (e.g. a retinide such as fenretinide) may be readily combined with the lipid matrix composition in any suitable amount, generally in a mole ratio of retinide:lipid matrix composition of from about 0.2:1 to about 2:1, more particularly about 0.4:1 to 1.5:1, and still more particularly about 0.6:1 to 1:1. The amount of active agent(s) in the composition may also be expressed as an amount by weight of the edible powder formulation, as further explained below.

Where two active agents are included, the combining step can be carried out by combining a first and second active agent with the non-acidic lipid matrix composition to form the viscous fluid. In the alternative, a first active agent can be combined with a first non-acidic lipid matrix composition as described herein; a second active agent combined with a second non-acidic lipid matrix composition as described herein (which may be the same as or different from the first); and the two precursors so formed then combined with one another to form the viscous fluid.

While lipid matrix compositions as described above are preferred for carrying out the present invention, the invention can also be carried out with liposome compositions. Liposomes suitable for use in the composition of the present invention include those composed primarily of vesicle-forming lipids, as exemplified by the phospholipids. The liposomes can also include other lipids incorporated into the lipid bilayers, with the hydrophobic moiety in contact with the interior, hydrophobic region of the bilayer membrane, and the head group moiety oriented toward the exterior, polar surface of the bilayer membrane. The vesicle-forming lipids are preferably ones having two hydrocarbon chains, typically acyl chains, and a head group, either polar or nonpolar. There are a variety of synthetic vesicle-forming lipids and naturally-occurring vesicle-forming lipids, including the phospholipids, such as phosphatidylcholine, phosphatidylethanolamine, phosphatidic acid, phosphatidylinositol, and sphingomyelin, where the two hydrocarbon chains are typically between about 14-22 carbon atoms in length, and have varying degrees of unsaturation. The above-described lipids and phospholipids whose acyl chains have varying degrees of saturation can be obtained commercially or prepared according to published methods. Other suitable lipids include glycolipids and sterols such as cholesterol. see, e.g., U.S. Pat. No. 6,355,268; see also U.S. Pat. Nos. 6,673,364; 6,660,525; and 5,773,027 (the disclosures of which applicants specifically intend be incorporated herein by reference).

3. Edible Powder Formulations.

In a preferred embodiment of the invention, the mixture or complex of active agent (such as retinide) and lipid matrix composition is mixed with additional ingredients to form a free-flowing, edible powder of solid particulate matter (e.g., as opposed to a liquid). Such additional ingredients include sweeteners, flours, humectants, etc. In general, such a composition may comprise or consist essentially of:

(a) from about 1 or 2 up to about 4, 6 or 10 percent by weight of active agent (such as retinide) (including a single active agent, or two or more active agents in combination);

(b) from about 5 or 10 up to about 30 or 40 percent by weight of lipid matrix composition as described above;

(c) optionally, but in some embodiments preferably, from about 1, 2, 5 or 10 up to about to 30 or 40 percent by weight of sweetener (lower amounts being possible by inclusion of high intensity sweeteners as discussed below);

(d) from about 20, 30 or 40 up to about 60, 70 or 80 percent by weight flour; and (e) optionally, from 0 or 1 up to about 10, 16 or 20 percent by weight of a humectant (as needed or desired depending upon choice of sweetener and other ingredients).

Additional optional ingredients may include small amounts of salt, colorants, preservatives, stabilizers, antimicrobials, anti-caking additives, etc., as is conventional in the art.

In one embodiment, where the active ingredients are fenretinide and PPMP in combination, the active ingredients are included in the combination at a weight ratio range of 20:1 to 1:4 (fenretinide:PPMP) and more preferably at a weight ratio range of 10:1 to 1:2 (fenretinide:PPMP).

Sweeteners that may be used in preparing formulations of the invention include, but are not limited to, sugars such as sucrose, dextrose, fructose, maltodextrin, glucose, tagatose, lactose, invert sugar, maltose, etc., as well as high intensity sweeteners such as sucralose, sodium cyclamate, sodium saccharin, aspartame, etc. All such sweeteners may be used alone or in combination with one another.

Any edible fine dry powder produced by grinding a nut, cereal grain or other source of plant starch or carbohydrate may be used as the flour in the present invention. Suitable flours include but are not limited to rice flour, potato flour, corn flour, masa corn flour, tapioca flour, buckwheat flour, wheat flour, oat flour, bean flour, barley flour rye flour, millet flour, sorghum flour, chestnut flour, and mixtures thereof. The flour may optionally have additional ingredients such as preservatives and flowing agents included therein.

Humectants may optionally be included in the composition where necessary or desired to, among other things, lower the $a_W$ of the composition. Examples of humectants include, but are not limited to, corn syrup, high fructose corn syrup, polyhydric alcohols (e.g., sorbitol, glycerol, xylitol and the like), polydextrose, combinations thereof, etc. In some embodiments, the compositions have an water activity (or "$a_W$") less than 0.85 (to reduce pathogen growth therein); in some embodiments the compositions have an $a_W$ less than 0.65 (to reduce growth of osmotolerant yeasts and molds therein).

Flavorants that may optionally be included in the composition include, but are not limited to: almond nut, amaraetto, anisette, banana, tapioca, brandy, cappuccino, mint, cinnamon, cinnamon almond, creme de menthe, orange, peppermint stick, pistachio, licorise, apple, chamomile, cinnamon spice, creme, vanilla, french vanilla, lemon, macadamia nut, orange, orange leaf, peach, strawberry, grape, raspberry, cherry, coffee, chocolate and the like, aroma enhancers such as acetaldehyde, herbs, spices, mocha, butternut, rum, hazelnut, horchata, dulche de leche, etc., as well as mixtures of these flavors. See, e.g., U.S. Pat. No. 6,207,206.

Compositions of the invention can be made by, first, combining an active agent (such as a retinide) with a lipid matrix composition as described above. The lipid matrix composition is preferably non-acidic or basic, and preferably contains less than 7 or 8 moles of water (and more preferably not more than 3 moles of water) per mole of lipid matrix. The combining step may be carried out by heating the lipid matrix composition to form a soft or viscious or oily composition and then stirring or mixing the active agent therein to form a soft or viscous or oily product. The viscous/oily product is then mixed with flour and optionally sweetener (and other optional ingredients as desired), with the mixing being carried out with sufficient shear stress (e.g., by stirring or blowing) to produce a flowable powder composition as described herein. For example, mixing can be carried out by pouring the flour (and optionally sweetener) into the viscous/oily product with concurrent stirring in a food processor, blender, commercial mixer or blender, or the like. The speed of the mixing apparatus can be varied as desired throughout the process: e.g., with mixing being carried out at a lower speed to initially combine the ingredients, and then the speed increased as desired to produce the flowable powder composition described herein.

The flowable powder may be packaged in bulk or unit dose containers such as packets or sealed cups for subsequent use, with unit dose containers preferably containing from 1 to 10 or 20 grams of the flowable powder.

The flowable powder may be consumed or administered per se to a subject. The flowable powder may, if desired, be caked or baked into a formed food product such as a cookie, wafer, or bar for subsequent consumption by a subject. The flowable powder may, if desired, be mixed with another liquid, solid, or semi-solid food or nutritional supplement for administration to a patient (examples including but not limited to oatmeal or other grain meals, pudding, ice creams, sorbet, apple sauce, liquid soy-based nutritional supplement compositions such as SLIM-FAST™ and fruit juice). Preferably the foods or compositions with which the powder is mixed do not contain lipid-matrix destabilizing agents such as milk fat (e.g., replacing milk fats with soy fats).

4. Treatment and Administration.

The present compositions and formulations can be administered for the treatment of hyperproliferative disorders such as tumors, cancers, and neoplastic disorders, as well as pre-malignant and non-neoplastic or non-malignant hyperproliferative disorders or for the treatment of other medical conditions in need of treatment, such as hypertension, infection, inflammation, graft versus host disease, etc.

Subjects to be treated by the compositions, formulations and methods described herein are, in general, mammalian subjects, including both human subjects and animal subjects such as dogs, cats, horses, etc. for veterinary purposes. The subjects are, in some embodiments, infant, juvenile, or geriatric subjects.

Examples of tumors, cancers, and neoplastic tissue that can be treated by the present invention include but are not limited to malignant disorders such as breast cancers; osteosarcomas; angiosarcomas; fibrosarcomas and other sarcomas; leukemias; lymphomas; sinus tumors; ovarian, uretal, bladder, prostate and other genitourinary cancers; colon, esophageal and stomach cancers and other gastrointestinal cancers; lung cancers; myelomas; pancreatic cancers; liver cancers; kidney cancers; endocrine cancers; skin cancers; and brain or central and peripheral nervous (CNS) system tumors, malignant or benign, including gliomas and neuroblastomas.

Examples of premalignant and non-neoplastic or non-malignant hyperproliferative disorders include but are not limited to myelodysplastic disorders; cervical carcinoma-in-situ; familial intestinal polyposes such as Gardner syndrome; oral leukoplakias; histiocytoses; keloids; hemangiomas; hyperproliferative arterial stenosis, inflammatory arthritis; hyperkeratoses and papulosquamous eruptions including arthritis. Also included are viral induced hyperproliferative diseases such as warts and EBV induced disease (i.e., infectious mononucleosis), scar formation, and the like. The methods of treatment disclosed herein may be employed with any subject known or suspected of carrying or at risk of developing a hyperproliferative disorder as defined herein.

As used herein, "treatment" of a hyperproliferative disorder refers to methods of killing, inhibiting or slowing the growth or increase in size of a body or population of hyperproliferative cells or tumor or cancerous growth, reducing hyperproliferative cell numbers, or preventing spread to other anatomic sites, as well as reducing the size of a hyperproliferative growth or numbers of hyperproliferative cells. As used herein, "treatment" is not necessarily meant to imply cure or complete abolition of hyperproliferative growths. As used herein, a treatment effective amount is an amount effective to result in the killing, the slowing of the rate of growth of hyperproliferative cells, the decrease in size of a body of hyperproliferative cells, and/or the reduction in number of hyperproliferative cells.

The therapeutically effective dosage of any one active agent, the use of which is in the scope of present invention, will vary somewhat from compound to compound patient to patient, and will depend upon factors such as the condition of the patient and the route of delivery. Such dosages can be determined in accordance with routine pharmacological procedures known to those skilled in the art, particularly in light of the disclosure provided herein. For fenretinide, a dose to achieve a plasma level of about 1 µM to 10 or 50 µM, or greater, is employed (e.g., an oral dose of 10 or 20 to 500 or 1000 mg of fenretinide).

Feeding of the compositions of the invention may be carried out by any of a variety of procedures. The subject may be fed the composition orally and directly. The composition may be diluted or combined in a food or beverage prior to feeding to a subject.

The feeding may be carried out by feeding the subject through a gastric, jejunal, naso-gastric or nasal-jejunal feeding tube, in which case feeding preferably involves (i) combining the dry powder with a preferably non-lipid matrix destabilizing liquid (e.g., one substantially free of milk fat) to produce a liquid composition, and then (ii) delivering the liquid composition to the subject through the feeding tube.

Particularly suitable subjects for administering or feeding the compositions described herein are infant, juvenile or geriatric subjects.

The compositions described herein may be used in combination therapies, such as described in B. Maurer et al., U.S. Pat. No. 6,368,831, or B. Maurer et al., U.S. Pat. No. 6,352,844, the disclosures of which are incorporated by reference herein in their entirety.

The present invention is explained further in the non-limiting Examples set forth below.

EXAMPLE 1

Oral Compositions of 4-HPR

The actual dose of 4-HPR to be delivered to patients will ultimately define the resulting mixture volume, once it is determined. These arbitrary values present 4-HPR doses of 0.5 to 2.5 grams per mixture volume.

A concentrated LXS-HPR mixture would be >1000 mg HPR per 10 cc. As awkward as this may be for typical dosage calculations, we usually describe [drug]-LXS ratios in terms of moles. This is because our prior work suggests that 1 mole of drug successfully interacts within the inclusion space of 1 mole of LXS. So, if we use a mole ratio of 0.8 (0.8 moles of drug per mole of LXS), the maximum concentrated dosage would be 397*0.8/2429, or 131 mg HPR per gram of LXS.

In reading Table 1, then, with a mole ratio of 0.8, 2.5 g of 4-HPR would complex with 19.09 g LXS with a resulting total volume of 17.18 ml, or approximately 1400 mg per 10 cc. The calculations for lower mole ratios are included.

Preferably, the LXS composition (in the form of an oil) is mixed with 4-HPR first. Once dissolved in the oil, a small initial amount of basic water (such as containing the bicarbonate of soda) is mixed in to the composition to soften the composition to a foam. The resulting foam may then be mixed with a suspension agent (e.g., SLIMFAST™ soy beverage or more water) via probe sonication. Alternatively, the composition containing 4-HPR or other medicinal agent in the LXS can be compounded directly with edible food compositions or excipients.

EXAMPLE 2

Improved Bioavailability of Oral 4-HPR Using LYM-X-SORB™ Lipid Matrix

LYM-X-SORB™ (Lymphatic Xenobiotic Absorbability) lipid matrix (also referred to as LXS™ herein) is a patented and proprietary technology of LYM-DRUG PRODUCTS, LLC and BioMolecular Products, Inc., Byfield, Mass., useful for increasing the oral bioavailability of water insoluble compounds. LXS™ is a non-liposomal, lipid-based, drug delivery system composed of FDA-accepted GRAS (Generally Regarded As Safe) lipids (lysophosphatidylcholine (LPC), monoglycerides (MG), and fatty acids (FA)). LXS™ acts as a "lipid-fingered glove" which wraps around the drug of interest in a 1:1 molar ratio. In the presence of sodium bicarbonate and bile salts, the LXS/drug matrix forms <10 nm size particles that are readily absorbed. Neither the LXS™ monomer, nor the LXS/drug matrix, damage intestinal villae. LXS™ has been demonstrated safe in a one-year double blind oral feeding trial in Cystic Fibrosis (CF) children (Lepage, et al. J Pediatr. 114:178-185, 2002.) Diverse, minimally-soluble, drugs have been shown to be compatible with LXS™, including 4-HPR (U.S. Pat. No. 4,874,795).

TABLE 1

4-HPR:LXS Mixture Concentrations

| 4-HPR:LXS Mole Ratio | wt 4-HPR (g) | wt Corresponding LXS (g) | Mixture Volume (cc) |
|---|---|---|---|
| 0.60 | 0.50 | 5.09 | 4.58 |
|  | 1.00 | 10.18 | 9.16 |
|  | 1.50 | 15.27 | 13.75 |
|  | 2.00 | 20.36 | 18.33 |
|  | 2.50 | 25.45 | 22.91 |
| 0.65 | 0.50 | 4.70 | 4.23 |
|  | 1.00 | 9.40 | 8.46 |
|  | 1.50 | 14.10 | 12.69 |
|  | 2.00 | 18.80 | 16.92 |
|  | 2.50 | 23.50 | 21.15 |
| 0.70 | 0.50 | 4.36 | 3.93 |
|  | 1.00 | 8.73 | 7.85 |
|  | 1.50 | 13.09 | 11.78 |
|  | 2.00 | 17.45 | 15.71 |
|  | 2.50 | 21.82 | 19.64 |
| 0.75 | 0.50 | 4.07 | 3.67 |
|  | 1.00 | 8.15 | 7.33 |
|  | 1.50 | 12.22 | 11.00 |
|  | 2.00 | 16.29 | 14.66 |
|  | 2.50 | 20.36 | 18.33 |
| 0.80 | 0.50 | 3.82 | 3.44 |
|  | 1.00 | 7.64 | 6.87 |
|  | 1.50 | 11.45 | 10.31 |
|  | 2.00 | 15.27 | 13.75 |
|  | 2.50 | 19.09 | 17.18 |

In beagle dogs, LXS™ increased the peak plasma concentration of 200 mg doses of 4-HPR by 5-fold, and increased mean area under the curve (AUC) by 4.2-fold compared to the current oral capsular formulation (of Gibbs)(U.S. Pat. No. 4,665,098). In single-dose experiments in healthy human volunteers, plasma concentrations equivalent to those obtained using the current capsular 4-HPR formulation were achieved using ⅕ the 4-HPR dose in a LXS™ formulation. These results suggested that a liquid formulation of 4-HPR with increased bioavailability might be possible using LXS™ technology.

Figure 1:
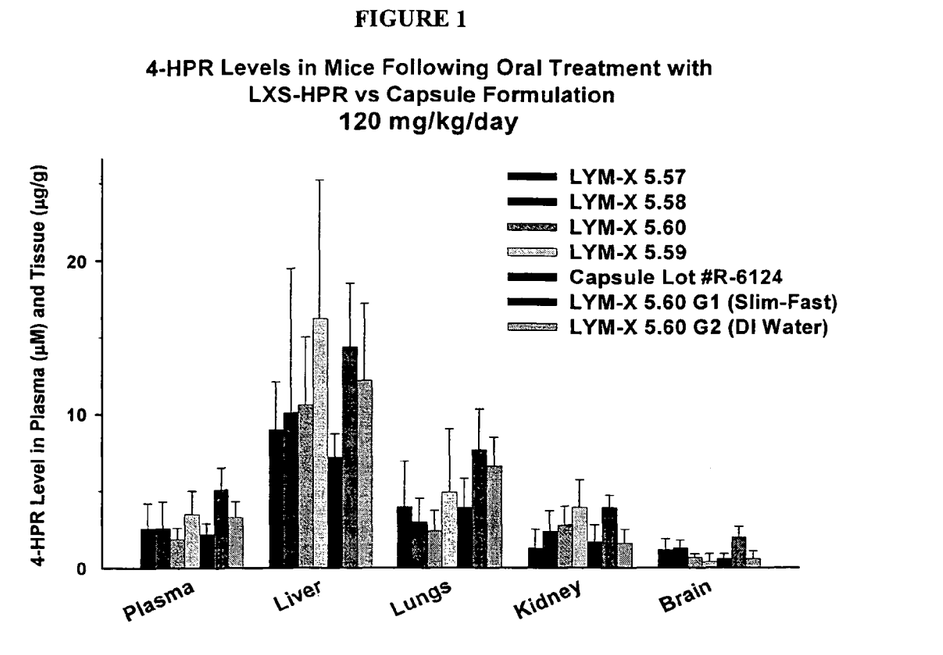
Figure 2:
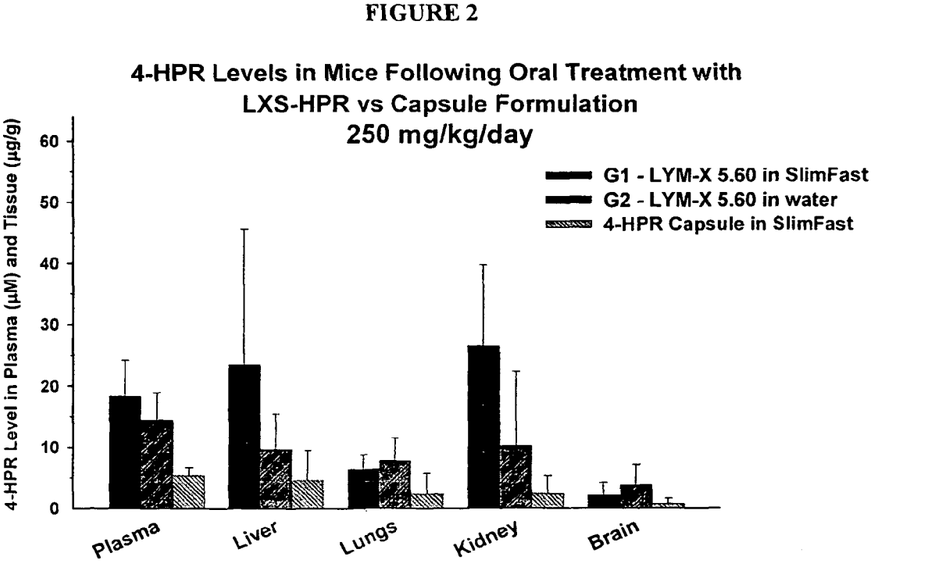
Figure 3:
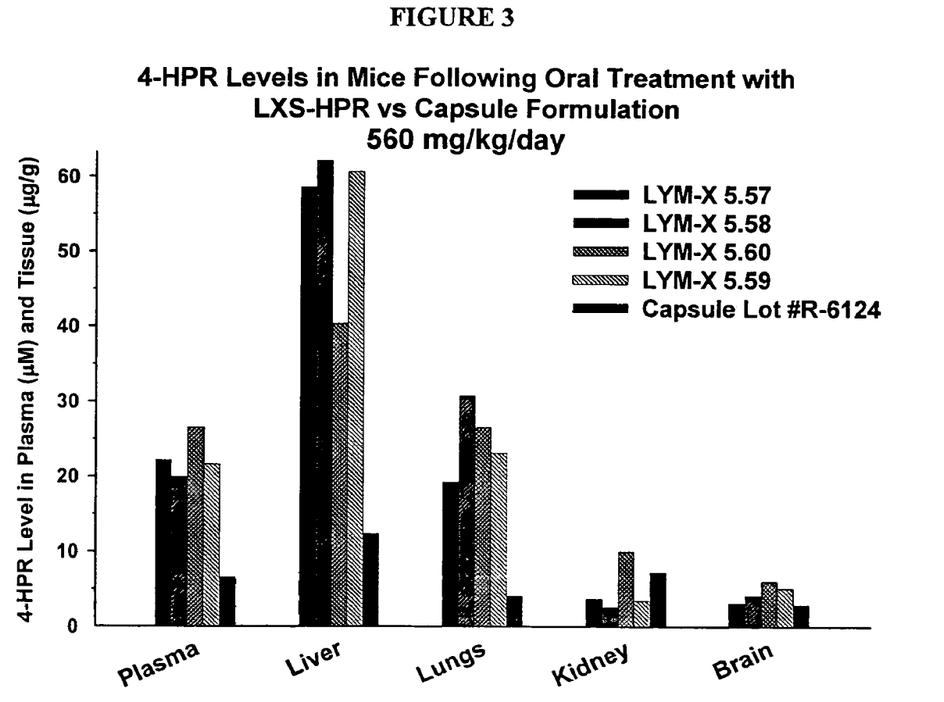

To test this hypothesis, we had various LXS™ compositions of 4-HPR prepared that varied in the LPC:MG:FA ratios of the LXS™ matrix. We then feed mice with equal doses of 4-HPR in the LXS™ compositions, or expressed as a slurry from the current oral 4-HPR capsules. Steady state plasma and tissue levels of 4-HPR were assayed after animal sacrifice. The results demonstrated that 4-HPR plasma and tissue levels were dose-dependent, and that certain LXS™ formulations obtained significantly higher steady-state 4-HPR plasma and tissues than those achieved by the current capsular formulation, especially at higher doses (FIGS. 1, 2, and 3). All animals completed the experiments. No obvious toxicities were observed. In FIG. 1:

LYM-X 5.57=1:2:4 lysophosphatidylcholine:monoglycerides:fatty acid (LPC:MG:FA);

LYM-X 5.58=1:4:2;

LYM-X 5.59=1:4:2 with some base (bicarb) added during processing in an amount sufficient to soften the oily mixture to a foam as discussed above;

LYM-X 5.60=1:3:3; and

G1, G2=LYM-X 5.60 in water or SLIMFAST™ soy beverage The LYMX-X-5.59 composition is currently preferred.

EXAMPLE 3

Powder Formulation Process

A 1:0.8 Mole ratio combination of LYM-X-SORB™ drug matrix compostition was combined with fenretinide in accordance with known techniques and as described in Example 1 above in a 1:0.8 Mole ratio to form an LXS/4-HPR complex. The lipid matrix is not acidified or significantly hydrated to form a protonated aqueous lipid matrix of predominantly hexagonal or inverse hexagonal phase. Rather, the lipid matrix is basic, minimally-hydrated, and of predominantly lamellar phase. The LXS/4-HPR is blended to an oil and stored at −20° C. The oil is ~88.8% (wt) LXS and 11.2% (wt) 4-HPR (1:0.8 mole ratio).

A food processor is used for the blending to a powder but this may be replaced by a much larger reactor vessel with internal chopper blades or other mixing device to process multiple kilos simultaneously. Either way, the flour and sugar are loaded into the blending vessel and mixed for ~1 minute or more at room temperature. The LXS/4-HPR is then loaded at ambient temperature as a semi-solid to the flour/sugar. Allowing the LXS/4-HPR to warm to room temperature for ~1 hour prior to loading provides a thick material capable of scooping in solid pieces similar to butter. The combination is then mixed at room temperature via the blending device (on high) for ~2-3 minutes or until no solid LXS/4-HPR is noted. The resulting powder is bright yellow and free flowing with mild agglomerations that are easily broken apart upon examination. This material is discharged and weighed into the respective containers. Constituent ranges are:

53.5% (wt) wheat flour,
19.6% (wt) granulated sugar,
23.8% (wt) LXS and
3.1% (wt) 4-HPR.

These weights, to date, have not had much discrepancy so the ranges are relatively tight (±1%) but in some preferred embodiments the final product may comprise at least 22-27% total lipid and 2.5-3.5% 4-HPR.

Salt and bicarbonate may be added in limited amounts (preferably not more than about 1%). Corn syrup may be added up to 15%, but in combination with 15% LXS the mixture becomes too thick for powder work.

The foregoing is illustrative of the present invention, and is not to be construed as limiting thereof. The invention is defined by the following claims, with equivalents of the claims to be included therein.

That which is claimed is:

1. An edible composition for oral delivery of an active agent, said composition comprising, in the form of a dry flowable powder:
   (a) from 1 to 20 percent by weight of a retinide;
   (b) from 5 to 40 percent by weight of non-acidic lipid matrix composition, said matrix composition comprising at least one fatty acid, at least one monoglyceride, and lysophosphatidylcholine, and said lipid matrix composition containing not more than 4 moles water per mole of lipid matrix;
   (c) from 1 to 30 percent by weight of sweetener;
   (d) from 20 to 80 percent by weight flour; and
   (e) from 0 to 16 percent by weight of a humectant.

2. The composition of claim 1, said lipid matrix composition comprising (i) at least one non-esterified fatty acid having 14 to 22, carbon atoms (ii) at least one monoglyceride which is a monoester of glycerol and a fatty acid having 14 to 22 carbon atoms, and (iii) lysophosphatidylcholine in which the fatty acid moiety has 14 to 22 carbon atoms, wherein said fatty acids and monoglycerides together comprise from 70 mole percent to 99 mole percent of said lipid matrix composition, the molar ratio of said fatty acids to the monoglycerides is from 2:1 to 1:2, and said lysophosphatidylcholine comprises from 1 mole percent to 30 mole percent of said lipid matrix composition.

3. The composition of claim 1, wherein said sweetener is selected from the group consisting of sucrose, dextrose, fructose, maltodextrin, glucose, tagatose, lactose, invert sugar, maltose, sucralose, sodium cyclamate, sodium saccharin, and aspartame.

4. The composition of claim 1, said flour selected from the group consisting of rice flour, potato flour, corn flour, masa corn flour, tapioca flour, buckwheat flour, wheat flour, oat flour, bean flour, barley flour, rye flour, millet flour, sorghum flour, chestnut flour, and mixtures thereof.

5. The composition of claim 1, said composition having a water activity ($a_W$) less than 0.85.

6. The composition of claim 1, wherein said humectant is included in said composition in an amount of at least 1% by weight and is selected from the group consisting of corn syrup, high fructose corn syrup, polyhydric alcohols, polydextrose, combinations thereof, and combinations thereof.

7. The composition of claim 1, said lipid matrix composition further comprising water in an amount not greater 3 moles water per mole lipid matrix.

8. The composition of claim 1, wherein said composition comprises:
   (a) from 2 to 6 percent by weight of a retinide;
   (b) from 10 to 30 percent by weight of said lipid matrix composition;
   (c) from 5 to 30 percent by weight of said sweetener; and
   (d) from 30 to 60 percent by weight flour.

9. A mixed food composition comprising the composition of claim 1 in combination with a food carrier.

10. The mixed food composition of claim 9, wherein said food carrier is selected from the group consisting of liquid soy-based nutritional supplement, oatmeal, pudding, ice creams, sorbet, apple sauce, and fruit juice.

11. The composition of claim 1, wherein said composition further comprises from 1 to 20 percent by weight of a glucosylceramide synthase inhibitor.

12. The composition of claim 11, wherein said retinide is fenretinide and said glucosylceramide synthase inhibitor is 1-phenyl-2-palmitoylamino-3 -morpholino-1-propanol (PPMP).

13. A method of making a composition of claim 1, comprising the steps of:
   combining at least one active agent with a non-acidic lipid matrix composition, said matrix composition comprising at least one fatty acid, at least one monoglyceride, and lysophosphatidylcholine, and said lipid matrix composition containing not more than 4 moles water per mole of lipid matrix to form a viscous fluid; and then
   mixing said viscous fluid with sweetener and flour with sufficient shear stress to produce a flowable powder composition according to claim 1.

14. The method of claim 13, wherein said retinide is fenretinide.

15. The method of claim 13, wherein said method further comprises combining a glucosylceramide synthase inhibitor with the non-acidic lipid matrix composition.

16. The method of claim 15, wherein said retinide is fenretinide and said glucosylceramide synthase inhibitor is 1-phenyl-2-palmitoylamino-3 -morpholino-1-propanol (PPMP).

17. The method of claim 15, wherein said combining step is carried out by combining a retinide and a glucosylceramide synthase inhibitor with said non-acidic lipid matrix composition to form said viscous fluid.

18. The method of claim 13, wherein said combining step is carried out by:
   combining a retinide with a non-acidic lipid matrix composition, said matrix composition comprising at least one fatty acid, at least one monoglyceride, and lysophosphatidylcholine, and said first lipid matrix composition containing not more than 4 moles water per mole of lipid matrix to form a first precursor fluid;
   combining a glucosylceramide synthase inhibitor with a second non-acidic lipid matrix composition, said matrix composition comprising at least one fatty acid, at least one monoglyceride, and lysophosphatidylcholine, and said lipid matrix composition containing not more than 4 moles water per mole of lipid matrix to form a second precursor fluid; and then
   combining said first precursor fluid and said second precursor fluid to form said viscous fluid.

19. The method of claim 18, wherein said retinide is fenretinide and said glucosylceramide synthase inhibitor is 1-phenyl-2-palmitoylamino-3-morpholino-1-propanol (PPMP).

* * * * *

UNITED STATES PATENT AND TRADEMARK OFFICE
CERTIFICATE OF CORRECTION

PATENT NO. : 7,780,978 B2
APPLICATION NO. : 11/170561
DATED : August 24, 2010
INVENTOR(S) : Maurer et al.

It is certified that error appears in the above-identified patent and that said Letters Patent is hereby corrected as shown below:

Column 20, Claim 13, Line 7: Please correct "combining at lease one active agent with" to read -- combining a retinide with --

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

PATENT NO. : 7,780,978 B2
APPLICATION NO. : 11/170561
DATED : August 24, 2010
INVENTOR(S) : Maurer et al.

Page 1 of 1

It is certified that error appears in the above-identified patent and that said Letters Patent is hereby corrected as shown below:

<u>On Title Page:</u>
Item (63) Related U.S. Application Data: Please correct "Jan. 30, 2004" to read -- Jan. 29, 2004 --

Column 1, Line 7: Please correct "Jan. 30, 2004" to read -- Jan. 29, 2004 --

Signed and Sealed this
Third Day of May, 2011

David J. Kappos
*Director of the United States Patent and Trademark Office*